US011208431B2

(12) United States Patent
Minato et al.

(10) Patent No.: US 11,208,431 B2
(45) Date of Patent: Dec. 28, 2021

(54) STABLE ISOTOPE-LABELED COMPOUNDS

(71) Applicant: ASKA PHARMACEUTICAL CO., LTD., Tokyo (JP)

(72) Inventors: Koichi Minato, Kawasaki (JP); Yusuke Ito, Kawasaki (JP)

(73) Assignee: ASKA PHARMACEUTIAL CO., LTD., Tokyo (JP)

( * ) Notice: Subject to any disclaimer, the term of this patent is extended or adjusted under 35 U.S.C. 154(b) by 0 days.

(21) Appl. No.: 16/763,616

(22) PCT Filed: Nov. 13, 2018

(86) PCT No.: PCT/JP2018/041947
§ 371 (c)(1),
(2) Date: May 13, 2020

(87) PCT Pub. No.: WO2019/098179
PCT Pub. Date: May 23, 2019

(65) Prior Publication Data

US 2020/0283469 A1 Sep. 10, 2020

(30) Foreign Application Priority Data

Nov. 15, 2017 (JP) ............................ JP2017-219740

(51) Int. Cl.
*C07J 1/00* (2006.01)
*G01N 30/04* (2006.01)
*G01N 33/74* (2006.01)
*G01N 30/02* (2006.01)

(52) U.S. Cl.
CPC ............ *C07J 1/0022* (2013.01); *G01N 30/02* (2013.01); *G01N 33/743* (2013.01); *C07B 2200/05* (2013.01); *G01N 2030/027* (2013.01); *G01N 2030/045* (2013.01)

(58) Field of Classification Search
CPC ... C07J 1/0011; C07J 1/0022; C07B 2200/05; G01N 2030/045
See application file for complete search history.

(56) References Cited

U.S. PATENT DOCUMENTS

2008/0176269 A1 7/2008 Mohler et al.
2015/0376225 A1* 12/2015 Dugar ..................... A61P 27/02 514/173
2017/0158730 A1* 6/2017 Dugar ..................... C07J 1/004

FOREIGN PATENT DOCUMENTS

WO 2013/171490 A1 11/2013

OTHER PUBLICATIONS

Landvatter, S.W. et al. "Stable Isotope Labeled Standards. Comparison of Deuterium, 13C and 15N Isotopic Labels in Mass Spec Internal Standards." 2016 IsoSciences (Year: 2016).*

Atzrodt, J. et al. "Synthesis of stable isotope labelled internal standards for drug-drug interaction (DDI) studies," Bioorganic & Medicinal Chemistry 20 (2012) 5658-5667. (Year: 2012).*

Furuta, T. et al. "Syntheses of stable isotope-labeled 6b-hydroxycortisol, 6b-hydroxycortisone, and 6b-hydroxytestosterone," Steroids 68 (2003) 693-703 (Year: 2003).*

4-Androsten-11b-ol-3,17-dione (2,2,4,6,6,16,16-D7, 98%), Cambridge Isotope Laboratories, Inc. Product code DLM-9697; Safety Data Sheet, Date of issue: Apr. 30, 2015, Revision date: May 8, 2017 (Year: 2017).*

Trafalis, D. et al. "Synthesis and evaluation of new steroidal lactam conjugates with aniline mustards as potential antileukemic therapeutics," Steroids 115 (2016) 1-8. Available online Jul. 26, 2016 (Year: 2016).*

Choe, Y.S. et al. "Synthesis of 11β-[18F]fluoro-5α-dihydrotestosterone and 11β-[18F]fluoro-19-nor-5α-dihydrotestosterone: preparation via halofluorination-reduction, receptor binding, and tissue distribution," J. Med. Chem. 1995, 38, 816-825 (Year: 1995).*

Du Toit et al. "Profiling adrenal 11β-hydroxyandrostenedione metabolites in prostate cancer cells, tissue and plasma: UPC2-MS/MS quantification of 11β-hydroxytestosterone, 11keto-testosterone and 11keto-dihydrotestosterone" Journal of Steroid Biochemistry and Molecular Biology, 2016, vol. 166, pp. 54-67.

Imamichi et al. "11-Ketotestosterone Is a Major Androgen Produced in Human Gonads" Journal of Clinical Endocrinology and Metabolism, 2016, vol. 101, No. 10, pp. 3582-3591.

International Search Report (PCT/ISA/210) dated Dec. 25, 2018, by the Japanese Patent Office as the International Searching Authority for International Application No. PCT/JP2018/041947.

Pretorius et al. "A new dawn for androgens: Novel lessons from 11-oxygenated C19 steroids" Molecular and Cellular Endocrinology, 2016, vol. 441, pp. 76-85.

Pretourius et al. "11-Ketotestosterone and 11-Ketodihydrotestosterone in Castration Resistant Prostate Cancer: Potent Androgens Which Can No Longer Be Ignored" PLOS One, 2016, vol. 11, No. 7, pp. e0159867/1-e0159867/17.

Quanson et al. "High-throughput analysis of 19 endogenous androgenic steroids by ultra-performance convergence chromatography tandem mass spectrometry" Journal of Chromatography B, 2016, vol. 1031, pp. 131-138.

Rege et al. "Liquid Chromatography—Tandem Mass Spectrometry Analysis of Human Adrenal Vein 19-Carbon Steroids Before and After ACTH Stimulation" J Clin Endocrinol Metab, 2013, 98(3): pp. 1182-1188.

(Continued)

*Primary Examiner* — Christopher Adam Hixson
*Assistant Examiner* — Michelle Adams
(74) *Attorney, Agent, or Firm* — Buchanan Ingersoll & Rooney PC

(57) ABSTRACT

Provided are a novel internal standard useful in the measurement of androgens, a method capable of measuring the androgen in a highly selective and highly sensitive (accurate) manner using liquid chromatography mass spectrometry with simplified pretreatments, and a method for diagnosis of a disease using the androgen measurement method. The novel stable isotope-labeled compound is synthesized by performing reduction reaction in a specific solvent. An androgen is measured using this novel stable isotope-labeled compound as an IS.

9 Claims, 2 Drawing Sheets

(56) References Cited

OTHER PUBLICATIONS

Shoppee et al. "Line widths of nuclear magnetic resonance signals of tertiary methyl groups" Tetrahedron, 1966, vol. 22, pp. 421-442.
Swart et al. "11β-Hydroxyandrostenedione, the product of androstenedione metabolism in the adrenal, is metabolized in LNCaP cells by 5α-reductase yielding 11β-hydroxy-5α-androstanedine" Journal of Steroid Biochemistry and Molecular Biology, 2013, vol. 138, pp. 132-142.
Extended European Search Report dated Jul. 29, 2021, by the European Patent Office in corresponding European Patent Application No. 18879038.0. (8 pages).
Du Toit et al., "Analysis of 52 C19 and C21 steroids by UPC2-MS/MS: Characterising the C11-oxy steroid metabolome in serum," Journal of Chromatography B, Jun. 13, 2020, vol. 1152, p. 122243.
Holland et al., "The mechanism of the microbial hydroxylation of steroids. Part 4. The C-6 β hydroxylation of androst-4-ene-3,17-dione and related compounds by Rhizopus arrhizus ATCC 11145," Canadian Journal of Chemistry, Mar. 1978, vol. 56, No. 5, pp. 694-702.

* cited by examiner

STABLE ISOTOPE-LABELED COMPOUNDS

TECHNICAL FIELD

The present invention relates to novel stable isotope-labeled compounds, to a method for measuring an androgen using the compounds as internal standards, to a method for diagnosis of a disease using the measurement method, to a biomarker for diagnosis, and to a method for synthesis of the compounds.

BACKGROUND ART

Androgens are a generic term for male hormones and substances having the same physiological actions as male hormones, and are thought of having actions such as the maintenance of reproductive organ functions, the embryonic sexual differentiation, the expression of secondary male sex characteristics, and the promotion of protein anabolism.

Their chemical structures are steroid derivatives. The major natural androgens are dehydroepiandrosterone (DHEA), its sulfate conjugate (DHEAS), testosterone (T) and androstenedione (A4). Dihydrotestosterone (DHT) that is the T metabolite is the most potent androgen.

The biosynthesis and secretion of the steroid hormones are regulated by hypothalamic-pituitary-adrenal (gonadal) endocrine system, and are precisely regulated by steroid biosynthetic enzymes in organs such as adrenal glands, testes and ovaries.

However, much remains uncertain as to why certain steroid hormones are produced and secreted in specific organs, and as to how catalytic enzymes are expressed and regulated.

In particular, little is known about the role of 11-ketotestosterone (11-KT) which is an endogenous androgen. Recent studies report that 11-KT has unique characteristics and is detected even in humans. Further, some studies suggest that this androgen can be a biomarker for various diseases such as prostate cancer (Non-Patent Literatures 1 to 5).

The in-vivo concentration of androgens is generally assayed by liquid chromatography mass spectrometry, for example, LC-MS/MS that uses a combination of a high-performance liquid chromatograph (HPLC) and a tandem quadrupole mass spectrometer (MS/MS). In the assay, an internal standard is used to correct the difference of response related to the difference of matrixes between the calibration sample and the actual sample. Some internal standards are, for example, stable isotope-labeled compounds which are exogenous, namely, progesterone-2,2,4,6,6,17α,21,21,21-$d_9$ (PROG-$d_9$), 4-pregnen-17α-ol-3,20-dione-2,2,4,6,6,21,21,21-$d_8$ (17OHPROG-$d_8$), testosterone-1,2-$d_2$ (T-$d_2$), cortisol-9,11,12,12-$d_4$ (cortisol-$d_4$), drospirenone and gestodene (Non-Patent Literature 6).

The measurement of an endogenous androgens using internal standards entails pretreatments for solid phase extraction and derivatization. Further, the solid phase extraction is wasteful (Non-Patent Literature 7).

CITATION LIST

Non-Patent Literature

Non-Patent Literature 1: J. Steroid Biochem Mol. Biol. 166 (2017) 54-67

Non-Patent Literature 2: J Clin Endocrinol Metab. 101 (10) (2016) 3582-3591

Non-Patent Literature 3: PLoS One 11 (7): e0159867. Doi: 10.1371/journal.pone.0159867

Non-Patent Literature 4: J. Steroid Biochem Mol. Biol. 138 (2013) 132-142

Non-Patent Literature 5: Molecular and Cellular Endocrinology 441 (2017) 76-85

Non-Patent Literature 6: J. Chromatography B, 1031, 131-138 (2016)

Non-Patent Literature 7: J. Clin. Endocrinol Metab. 98: 1182-1188 (2013)

SUMMARY OF INVENTION

Technical Problem

Previously, only testosterone and dihydrotestosterone can be evaluated total androgen activity. However, the present inventors have found that diseases associated with androgens will be more elucidated, and the pharmacological effects of drugs on such diseases will be evaluated more accurately by assaying, in addition to the measurement of these androgens, the in-vivo concentrations of androgenic active metabolite 11-ketodihydrotestosterone (11-KDHT), its precursors 11-ketoandrostenedione (11-KA4) and 11-ketotestosterone (11-KT), and transient metabolite (intermediate metabolite) 11β-hydroxytestosterone (11-OHT). The present inventors then carried out studies directed to the development of a method for the measurement of these androgens.

The 11-oxygenated C19 steroids (11-ox C19) such as 11-KDHT, 11-KA4 and 11-KT mentioned above are a generic term for androgens oxidized at the 11-position. These androgens have been studied in fishes in the past, and are recently detected in the bodies of mammals including humans. Their roles attract attention. While measurement methods using LC-MS/MS and UPLC-MS/MS have been reported, these methods do not use a stable isotope-labeled compound as an internal standard and thus may not accurately determine the amounts of 11-ox C19.

When PROG-$d_9$, 17OHPROG-$d_8$, T-$d_2$, cortisol-$d_4$, drospirenone and gestodene are used as internal standards, the retention time of these stable isotope-labeled compounds differs from that of the analytes, and thus it is impossible to sufficiently correct the matrix effects on the endogenous analytes.

Further, there are no internal standards useful for the measurement of 11-KA4, 11-KT and 11-OHT, and stable isotope-labeled compounds of these androgens are hardly available. The present inventors then attempted to synthesize such labeled compounds and encountered great difficulties. Specifically, the present inventors attempted to synthesize a stable isotope-labeled compound of an androgen by deuterium labeled androgen, and encountered difficulties in the specific deuterium labeling positions of the androgen. Further, the present inventors made an attempt to synthesize stable isotope-labeled androgen using a deuterated compound as the starting material, but could not synthesize the labeled androgen easily due to the detachment of deuterium or the occurrence of stereoisomers during the synthesis. In particular, the reduction reaction for obtaining [2,2,4,6,6,16,16-$D_7$] 11-ketotestosterone (11-KT-d7) from [2,2,4,6,6,16,16-$D_7$] 11-ketoandrostenedione (11-KA4-d7), when performed under the usual conditions, resulted in the occurrence of stereoisomers and did not afford 11-KT-d7 in the desired yield. To prevent stereoisomerization, the present inventors tried biosynthesis using rat testis microsomes. This attempt resulted in a low yield compared to the above method, and the amount which was usable per reaction was small (about 1/10000 of the chemical synthesis).

A derivatizing reagent that has been labeled with a stable isotope is used in the derivatization reaction of an analyte to synthesize a stable isotope-labeled derivative thereof. However, this method involves complicated operations for pretreatments. Further, the oxime derivatization on the carbonyl group that is common to the structures of all kinds of analytes produces stereoisomeric derivatives and gives rise to peak splitting. Therefore, in the case where analytes have similar m/z or structures, the spectrogram shows complicated peak separations from the peaks of other analytes or other endogenous steroids in the matrix due to the oxime derivatization, making the analysis complicated or impossible.

An objective of the present invention is to provide novel internal standards useful in the measurement of androgens.

Another objective of the present invention is to provide a method capable of measuring androgens in a highly selective and highly sensitive (accurate) manner using liquid chromatography mass spectrometry, in particular LC-MS/MS, with simplified pretreatments.

A further objective of the present invention is to provide a method for diagnosis using the above androgen measurement method.

Solution to Problem

The present inventors carried out extensive studies to achieve the above objectives, and have been successful in synthesizing novel stable isotope-labeled compounds which are usable as internal standards in the measurement of androgens, efficiently by performing reduction reaction in a specific solvent. The present inventors have found that by using this novel stable isotope-labeled compounds as internal standards, androgens can be measured in a highly selective and highly sensitive (accurate) manner with simplified pretreatments. Further, using this measurement method, the present inventors have measured androgens in healthy subjects and in patients with benign prostatic hyperplasia, prostate cancer, castration-resistant prostate cancer, polycystic ovary syndrome, diabetes mellitus or diabetes mellitus nephropathy, and have found that the levels of 11-ketoandrostenedione, 11-ketotestosterone, 11β-hydroxytestosterone and 11β-hydroxyandrostenedione are lower or higher (particularly, higher) in the patients than in the healthy subjects.

The present inventors have completed the present invention based on the above findings.

Specifically, aspects of the present invention reside in the following.

[1]

Stable isotope-labeled compounds represented by any one formula selected from the group consisting of Chemical Structure Formulae (I) to (III) below:

(I)

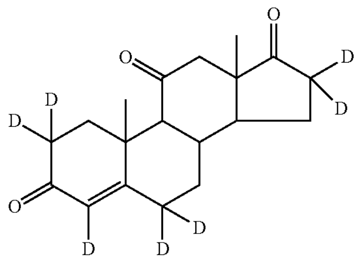

-continued (II)

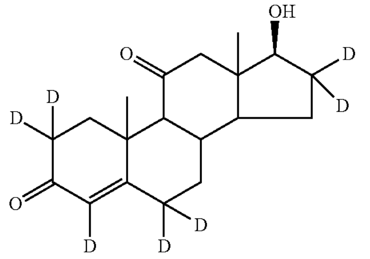

(III)

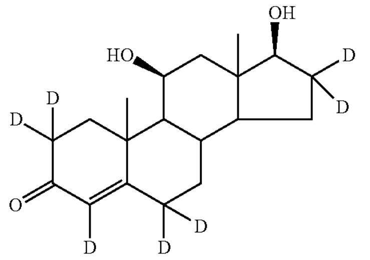

wherein D denotes deuterium.

[2]

A method for measuring androgens in a sample by liquid chromatography mass spectrometry, wherein the stable isotope-labeled compounds described in the above item [1] or a stable isotope-labeled compound of Formula (IV) described in the following item [11] is used as an internal standard.

[3]

The method described in the above item [2], wherein the method comprises the following procedures:

(Procedure 1) dissolving an androgen as an analyte into a solvent to prepare an analyte standard reference solution;

(Procedure 2) dissolving the stable isotope-labeled compound described in the above item [1] or the stable isotope-labeled compound of Formula (IV) described in the following item [11] into a solvent to prepare an internal standard reference solution;

(Procedure 3) combining a sample with the internal standard reference solution prepared in described above (Procedure 2) and a solvent to prepare an analyte concentration measurement sample;

(Procedure 4) combining the sample with the analyte standard reference solution prepared in described above (Procedure 1) and the internal standard reference solution prepared in described above (Procedure 2) to prepare a spike recovery test sample; and (Procedure 5) analyzing each of the analyte concentration measurement sample prepared in described above (Procedure 3) and the spike recovery test sample prepared in described above (Procedure 4) by liquid chromatography mass spectrometry.

[4]

The method described in the above item [2] or [3], wherein described above androgen is at least one selected from the group consisting of 11-ketoandrostenedione, 11-ketotestosterone, 11β-hydroxytestosterone, 11-ketodihydrotestosterone, testosterone, dihydrotestosterone and 11β-hydroxyandrostenedione.

[5]

The method described in the above item [3] or [4], wherein the concentration of the androgen in the analyte standard reference solution described in described above (Procedure 1) is 0.01 to 20 ng/mL.

[6]

The method described in any one of the above items [3] to [5], wherein the concentration of the stable isotope-labeled compound in the internal standard reference solution described above (Procedure 2) is 10 ng/mL.

[7]

A method for diagnosis of at least one of benign prostatic hyperplasia, prostate cancer, castration-resistant prostate cancer, polycystic ovary syndrome, diabetes mellitus and diabetes mellitus nephropathy, the method comprising measuring at least one of 11-ketoandrostenedione, 11-ketotestosterone, 11β-hydroxytestosterone and 11β-hydroxyandrostenedione in a sample using the method described in any one of the above items [2] to [6].

[8]

A method for diagnosis of prostate cancer or castration-resistant prostate cancer, the method comprising measuring 11-ketoandrostenedione in a sample using the method described in any one of the above items [2] to [6].

[9]

A biomarker comprising any of 11-ketoandrostenedione, 11-ketotestosterone, 11β-hydroxytestosterone and 11β-hydroxyandrostenedione, for diagnosis of at least one of benign prostatic hyperplasia, prostate cancer, castration-resistant prostate cancer, polycystic ovary syndrome, diabetes mellitus and diabetes mellitus nephropathy.

[10]

A biomarker comprising 11-ketoandrostenedione for diagnosis of prostate cancer or castration-resistant prostate cancer.

[11]

A method for producing a stable isotope-labeled compound described in the above item [1], comprising any one step selected from the group consisting of the following steps:

(Step 1) subjecting a compound represented by Formula (IV) below:

(IV)

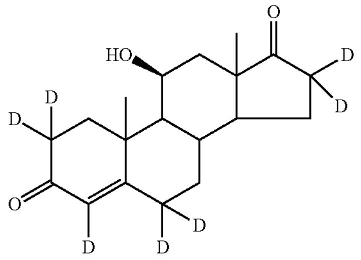

to an oxidation reaction to give a compound represented by Formula (I) below:

(I)

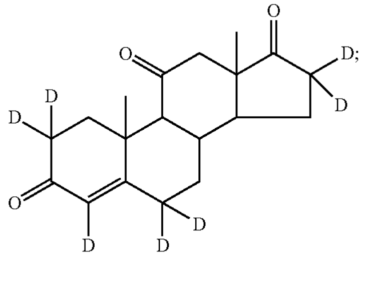

(Step 2) dissolving the compound of Formula (I) above into a super-dehydrated solvent and then subjecting it to a reduction reaction using a reducing agent dissolved in a super-dehydrated solvent to give a compound represented by Formula (II) below:

(II)

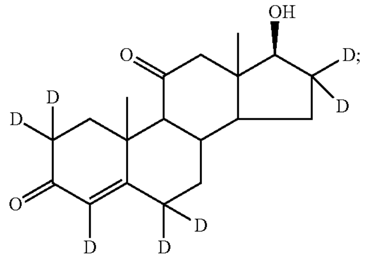

and (Step 3) dissolving the compound of Formula (IV) above into a super-dehydrated solvent and then subjecting it to a reduction reaction using a reducing agent dissolved in a super-dehydrated solvent to give a compound represented by Formula (III) below:

(III)

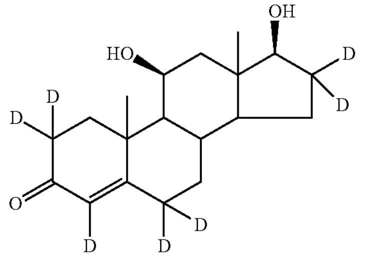

(in the above Formulae, D denotes deuterium).

Advantageous Effects of Invention

The liquid chromatography mass spectrometry using the stable isotope-labeled compounds of the present invention as internal standards enable highly selective and highly sensitive measurement of androgens, in particular, 11-ketoandrostenedione (11-KA4), 11-ketotestosterone (11-KT), 11β-hydroxytestosterone (11-OHT) and 11β-hydroxyandrostenedione (11-OHA4). The stable isotope-labeled compounds of the present invention make it possible to clarify the in-vivo metabolic flow (synthesis rates and loss rates) of androgens. In particular, positions at which the stable isotope-labeled compounds of the present invention are deuterated, that is, the labeled positions are clear, and this fact is advantageous in estimating the structures of metabolites. Further, the use of the stable isotope-labeled compounds of the present invention as internal standards allows measurements to be performed with simplified pretreatments.

Further, the present invention enables the diagnosis of benign prostatic hyperplasia, prostate cancer, castration-resistant prostate cancer, polycystic ovary syndrome, diabetes mellitus and diabetes mellitus nephropathy, in particular, the diagnosis of prostate cancer and castration-resistant prostate cancer.

According to the synthesis method of the present invention, the use of a super-dehydrated organic solvent in the reduction reaction suppresses the detachment of deuterium from the deuterated raw compound and the occurrence of stereoisomers, and allows a stable isotope-labeled compound of the present invention to be obtained in a good yield.

DESCRIPTION OF EMBODIMENTS

Figure 1:
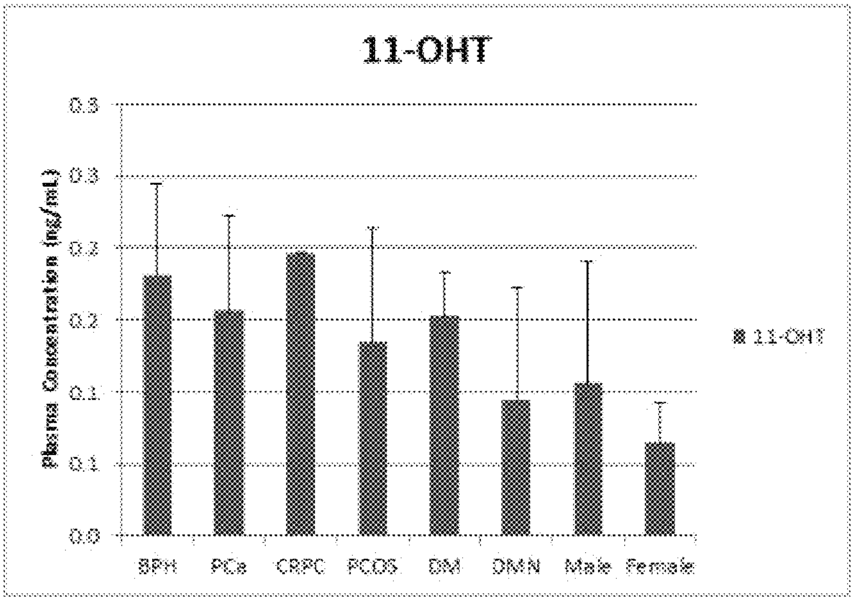
FIG. 1 shows the plasma 11-OHT concentrations in healthy human and patients with diseases

A stable isotope-labeled compound of the present invention is represented by any one formula selected from the group consisting of the chemical structures described in the item [1] hereinabove. The names and abbreviations of the compounds represented by the above chemical structures are described in the following table.

[Table 1]

TABLE 1

Names and abbreviations of compounds represented by chemical structure formulae of the present invention

| Chemical structure formulae | Names | Abbreviations |
|---|---|---|
| (I) | [2, 2, 4, 6, 6, 16, 16-$D_7$] 11-ketoandrostenedione | 11-KA4-d7 |
| (II) | [2, 2, 4, 6, 6, 16, 16-$D_7$] 11-ketotestosterone | 11-KT-d7 |
| (III) | [2, 2, 4, 6, 6, 16, 16-$D_7$] 11β-hydroxytestosterone | 11-OHT-d7 |

The stable isotope-labeled compounds of the present invention may be used as an internal standard for the measurement of an androgen in a sample by liquid chromatography mass spectrometry (LC-MS).

The stable isotope-labeled compound of the present invention may be used according to conventional procedures using liquid chromatography mass spectrometry, for example, according to the procedures described in the item [3] hereinabove.

The androgen that is the analyte in the measurement method of the present invention is not particularly limited and may be endogenous or exogenous. Examples thereof include 11-ketoandrostenedione (11-KA4), 11-ketotestosterone (11-KT), 11β-hydroxytestosterone (11-OHT), 11-ketodihydrotestosterone (11-KDHT), testosterone (T), dihydrotestosterone (DHT) and 11β-hydroxyandrostenedione (11-OHA4).

In particular, as the analyte, 11-ketoandrostenedione (11-KA4), 11-ketotestosterone (11-KT), 11β-hydroxytestosterone (11-OHT), 11-ketodihydrotestosterone (11-KDHT), testosterone (T) and dihydrotestosterone (DHT) are preferable, and 11-ketoandrostenedione (11-KA4), 11-ketotestosterone (11-KT) and 11β-hydroxytestosterone (11-OHT) are more preferable, for the reason that these analytes may be measured with high selectivity and high sensitivity (accuracy).

When, in particular, 11-KA4-d7 is used as the internal standard, the analyte is preferably 11-ketoandrostenedione (11-KA4); when 11-KT-d7 is used as the internal standard, the analyte is preferably 11-ketotestosterone (11-KT); when 11-OHT-d7 is used as the internal standard, the analyte is preferably 11β-hydroxytestosterone (11-OHT); when 11-OHA4-d7 is used as the internal standard, the analyte is preferably 11β-hydroxyandrostenedione (11-OHA4); when T-d3 is used as the internal standard, the analyte is preferably testosterone (T); and when DHT-d3 is used as the internal standard, the analyte is preferably dihydrotestosterone (DHT).

In the present invention, the analyte may be one, or two or more kinds of androgens. In the present invention, two or more kinds of androgens may be measured at one time. In this case, two or more kinds of the stable isotope-labeled compounds of the present invention may be used as the internal standards in combination with one another, and/or the stable isotope-labeled compound(s) of the present invention may be used together with other internal standards, for example, T-d3, DHT-d3 or 11-OHA4-d7.

The solvents used in the above Procedures 1 to 3 are not particularly limited and may be any solvents usually used in the preparation of samples for liquid chromatography mass spectrometry. Examples thereof include organic solvents such as acetonitrile, acetone, 1,4-dioxane, tetrahydrofuran, 1-propanol and 2-propanol. Acetonitrile is preferable for the reason that highly selective and highly sensitive (accurate) measurement is feasible.

The concentration of the androgen in the analyte standard reference solution in the above Procedure 1 is not particularly limited, but is preferably 0.01 to 100 ng/mL, more preferably 0.01 to 50 ng/mL, and particularly preferably 0.01 to 20 ng/mL for the reason that highly selective and highly sensitive (accurate) measurement is feasible.

The concentration of the stable isotope-labeled compound in the internal standard reference solution in the above Procedure 2 is not particularly limited, but is preferably 10 ng/mL, more preferably 1 ng/mL, and particularly preferably 0.5 ng/mL for the reason that highly selective and highly sensitive (accurate) measurement is feasible.

In the present invention, the analysis of an androgen by liquid chromatography mass spectrometry includes the detection and/or the quantification of the androgen.

The liquid chromatography mass spectrometry (LC-MS) used in the present invention is an analytical method which involves a combination of a liquid chromatograph and a mass spectrometer. Examples thereof include LC-MS/MS, LC-ESI-MS/MS and LC-APCI-MS/MS, with LC-MS/MS being preferable. The measurement itself may be performed in a common manner.

The ionization in LC-MS may include, for example, atmospheric pressure chemical ionization, ESI, APPI and the like. In particular, positive ion mode ESI is desirable.

The mass spectrometry section may include, for example, a magnetic field analyzer, a quadrupole analyzer, a time-of-flight analyzer, etc. In the present invention, a quadrupole analyzer is preferably used for the reason that it offers good quantitative performance, wide dynamic range and good linearity.

For example, the ion detection in the quantification may include selected ion monitoring in which only the target ions are detected selectively, or selected reaction monitoring (SRM) in which one type of ions that have been generated in the first mass spectrometry section is selected as precursor ions, and product ions resulting from the cleavage of the precursor ions are detected in the second mass spectrometry section. In the present invention, the measurement preferably involves SRM for the reason that the selectivity is increased and noises are reduced, and consequently the signal/noise ratio is enhanced.

In the measurement method of the present invention, the "sample of interest" is not particularly limited and may be of biological origin, environmental origin or origin from industrial products. Examples of the samples of biological origin include blood, saliva, tear, sweat, urine, feces, bile, tissues, living cells, tissue or cell cultures, preparations obtained from organs in animals including humans, and plant extracts. Examples of the samples of environmental origin include soil, sewage, waste water, river water and sea water. Examples of the samples of origin from industrial products include foodstuffs and pharmaceuticals. In particular, some preferred samples of biological origin are blood, saliva, urine, tissues and living cells of animals including humans; some preferred samples of environmental origin are waste water and river water; and some preferred samples of origin from industrial products are pharmaceuticals.

The measurement method of the present invention may be used to diagnose at least one of benign prostatic hyperplasia, prostate cancer, castration-resistant prostate cancer, polycystic ovary syndrome, diabetes mellitus and diabetes mellitus nephropathy (hereinafter, also collectively referred to as "differential target diseases"), preferably prostate cancer or castration-resistant prostate cancer, by measuring at least one of 11-ketoandrostenedione, 11-ketotestosterone, 11β-hydroxytestosterone and 11β-hydroxyandrostenedione (hereinafter, also collectively referred to as "inventive biomarkers"), preferably 11-ketoandrostenedione, in a sample.

Concretely, the presence or absence of a differential target disease may be diagnosed by measuring at least one of the inventive biomarkers in each sample from a subject and a control by the measurement method of the present invention, and comparing the value measured of the subject to the value measured of the control. When, for example, the value measured of the subject is statistically significantly incomparable, lower or higher, in particular higher, to the value measured of the control, the subject can be diagnosed as being affected by the differential target disease.

In the diagnostic method of the present invention, the term "subject" means a human or other animals, and the term "control" means a human or other animals diagnosed as not being affected by the differential target disease. The "sample" may include, for example, blood, saliva, tear, sweat, urine, feces, bile, tissues, living cells, or cell culture, or preparations obtained from an organ.

In the present invention, 11-ketoandrostenedione, 11-ketotestosterone, 11β-hydroxytestosterone and 11β-hydroxyandrostenedione, in particular, 11-ketoandrostenedione, may be used as biomarkers for diagnosis of at least one differential target disease, in particular, prostate cancer or castration-resistant prostate cancer.

The present invention also pertains to a measurement kit for use in the measurement method of the present invention which includes the stable isotope-labeled compound according to the present invention.

The present invention also pertains to a diagnostic kit for use in the diagnostic method of the present invention which includes the stable isotope-labeled compounds according to the present invention.

The kits for use in the methods of the present invention include the stable isotope-labeled compounds of the invention, and may further include at least one selected from buffers, acids, bases, alcohols, androgens such as the biomarkers of the present invention, syringes and a document describing the measurement procedures. In addition, the kit for use in the diagnostic method of the present invention may further include a document describing the criteria.

More specifically, the "diagnostic kit" of the present invention includes a means that is necessary for diagnosis of a differential target disease by comparing a measured value of at least one inventive biomarker present in a sample from a subject to measured values of the at least one inventive biomarker present in samples from a control and a patient with the differential target disease, for example, includes a sampling tool, a column cartridge and the like as means for measuring at least one inventive biomarker present in a sample from a subject, and a comparison table of measured values each of controls and patients with the differential target disease as means for comparing a measured value of at least one inventive biomarker present in a sample from a subject to measured values of at least one inventive biomarker present in samples from a control and a patient with the differential target disease. In particular, the comparison table is particularly useful because the diagnosis of a differential target disease is feasible without relying on the judgment of a physician.

The present invention also pertains to a method for screening a therapeutic or prophylactic agent for a differential target disease, in particular prostate cancer or castration-resistant prostate cancer, which includes measuring at least one inventive biomarker, in particular 11-ketoandrostenedione, in a sample using the measurement method of the present invention.

In particular, the present invention pertains to a method for screening a therapeutic or prophylactic agent for prostate cancer or castration-resistant prostate cancer, which includes measuring 11-ketoandrostenedione in a sample using the measurement method of the present invention.

The stable isotope-labeled compounds of the present invention may be efficiently synthesized by the method described above [11]. In the method described above [11], specifically, the reduction reaction is performed in a super-dehydrated organic solvent. This condition suppresses the detachment of deuterium from the deuterated raw compound and the occurrence of stereoisomers, and allows a stable isotope-labeled compound of the present invention to be obtained in a good yield.

In Step 1 described above [11], the oxidation reaction is not particularly limited as long as the hydroxyl group can be oxidized into the carbonyl group. Examples of such oxidation reactions include Dess-Martin oxidation, Jones oxidation and Swern oxidation. Dess-Martin oxidation is preferable.

Dess-Martin oxidation may be carried out using a conventional technique. For example, this oxidation reaction may be performed in the following manner.

First, the compound of Formula (IV): [2,2,4,6,6,16,16-$D_7$] 11β-hydroxyandrostenedione (11-OHA4-d7) is dissolved into a solvent to give an 11-OHA4-d7 solution. Dess-Martin oxidation reagent is added to the 11-OHA4-d7 solution, and for example the reaction is performed by stirring the mixture at room temperature for an appropriate amount of time, for example, about 10 to about 60 minutes, preferably about 30 minutes. After the completion of the reaction, the compound (11-KA4-d7) of Formula (I) that has resulted from the reaction is isolated from the reaction solution by a conventional technique.

The above Dess-Martin oxidation reagent may be a conventional reagent, for example, 1,1,1-triacetoxy-1,1-dihydro-1,2-benziodoxol-3(1H)-one which is called Dess-Martin Periodinane.

Further, the above solvent is not particularly limited as long as it is usually used in Dess-Martin oxidation. For example, an organic solvent, preferably dichloromethane, may be used.

The reduction reaction in Steps 2 and 3 described above [11] is not particularly limited as long as the carbonyl group is reduced to the hydroxyl group. Examples of such reduction reactions include reduction using sodium borohydride ($NaBH_4$) as a reducing agent, catalytic reduction, and reduction using lithium aluminum hydride ($LiAlH_4$). Reduction using sodium borohydride as a reducing agent is preferable.

The super-dehydrated solvent used in these steps is not particularly limited as long as the water content in the solvent is as low as 0.001% (10 ppm) or below. Examples thereof include super-dehydrated organic solvents selected from alcohols such as methanol and ethanol; and aromatic hydrocarbons such as benzene, toluene, ethylbenzene and xylene. For the reason that the stable isotope-labeled compound of the present invention can be obtained in a good yield, super-dehydrated methanol and super-dehydrated benzene are preferable, and it is particularly preferable to dissolve the deuterated raw compound into a super-dehydrated aromatic hydrocarbon, especially super-dehydrated benzene, and it is also preferable that the reducing agent be dissolved into a super-dehydrated alcohol, especially super-dehydrated methanol.

In the reduction reaction in Steps 2 and 3 described above, a solvent that is not super-dehydrated may be used in combination with the super-dehydrated solvent. In particular, such a solvent that is not super-dehydrated is preferably used in the process in which the deuterated raw compound is dissolved into the super-dehydrated solvent.

Examples of the solvents that are not super-dehydrated include pyridine.

The reduction with sodium borohydride as the reducing agent in Steps 2 and 3 described above [11] may be carried out using a conventional technique. The reduction may be performed in the following manner.

Namely, Step 2 starts with dissolving the compound (11-KA4-d7) (I) into a super-dehydrated solvent to form an 11-KA4-d7 solution. Separately, sodium borohydride is dissolved into a super-dehydrated solvent to give a $NaBH_4$ solution. The $NaBH_4$ solution is added dropwise to the 11-KA4-d7 solution over a period of, for example, about 1 to about 10 minutes, preferably about 5 minutes, and then the reaction is performed by, for example, stirring the mixture under ice cooling for a proper time, for example, about 10 to about 60 minutes, preferably about 30 minutes. After the completion of the reaction, the compound (11-KT-d7) (II) that has resulted from the reaction is isolated from the reaction solution by a conventional technique.

Step 3 starts with dissolving the compound (11-OHA4-d7) (IV) into a super-dehydrated solvent to form an 11-OHA4-d7 solution. Separately, sodium borohydride is dissolved into a super-dehydrated solvent to give a $NaBH_4$ solution. The $NaBH_4$ solution is added dropwise to the 11-OHA4-d7 solution over a period of, for example, about 5 to about 30 minutes, preferably about 15 minutes, and then the reaction is performed by, for example, stirring the mixture under ice cooling for a proper time, for example, about 10 to about 100 minutes, preferably about 1 hour. After the completion of the reaction, the compound (11-OHT-d7) (III) that has resulted from the reaction is isolated from the reaction solution by a conventional technique.

EXAMPLES

The present invention will be described in greater detail by presenting Examples below. However, it should be construed that the scope of the present invention is not limited to such Examples. The apparatuses and the materials used in Examples are described below.

1. Synthesis of Stable Isotope-Labeled Compounds

11-KA4-d7, 11-KT-d7 and 11-OHT-d7 were synthesized.

(1) Materials

The following materials were used.

[Table 2]

TABLE 2

| Starting material | |
|---|---|
| Name (abbreviation) | Manufacturer |
| [2, 2, 4, 6, 6, 16, 16-D7] 11β-Hydroxyandrostenedione (11-OHA4-d7) | CDN ISOTOPES |

[Table 3]

TABLE 3

| Standard materials | | |
|---|---|---|
| Names (abbreviations) | Manufacturers | Remarks |
| 11-Ketotestosterone (11-KT) | Steraloids | Cat No A6720-000 |
| 11β-Hydroxyandrostenedione (11-OHA4) | Steraloids | Cat No A6630-000 |
| 11-Ketoandrostenedione (11-KA4) | Steraloids | Cat No A7250-000 |
| 11β-Hydroxytestosterone (11-OHT) | Steraloids | Cat No A5760-000 |

[Table 4]

TABLE 4

| Reagents and other materials | | | |
|---|---|---|---|
| Names (abbreviations) | Grades | Manufacturers | Remarks |
| Dess-Martin periodate | — | KANTO CHEMICAL CO., INC. | — |
| Sodium borohydride (NaBH4) | — | Wako Pure Chemical Industries, Ltd. | For chemical use |

TABLE 4-continued

| Reagents and other materials | | | |
|---|---|---|---|
| Names (abbreviations) | Grades | Manufacturers | Remarks |
| Methanol (super-dehydrated) | Reagent | Wako Pure Chemical Industries, Ltd. | For organic synthesis |
| Benzene | — | Wako Pure Chemical Industries, Ltd. | — |
| Benzene (super-dehydrated) | Reagent | Wako Pure Chemical Industries, Ltd. | For organic synthesis |
| Acetone | Special grade | Wako Pure Chemical Industries, Ltd. | — |
| Dichloromethane | Special grade | Wako Pure Chemical Industries, Ltd. | — |
| Pyridine | Special grade | Wako Pure Chemical Industries, Ltd. | — |
| Acetic acid | Special grade | Wako Pure Chemical Industries, Ltd. | For precise analysis |

The reagents that were used were special grade reagents, HPLC standard reagents, or higher grade reagents. The water that was used was purified water which had been treated with ultrapure water production equipment.

(2) Facilities and Equipments

The following facilities and equipments were used.

[Table 5]

TABLE 5

| Reagents and other materials | | | |
|---|---|---|---|
| Names | Models | Manufacturers | Device Nos. |
| NMR | JNM-ECS400 | JEOL Ltd. | M/EQM/275 |
| LC/MS/MS System-6 | ACQUITY UPLC | Waters | m/EQM/215 |
| | XevoQ-TOF | Waters | |
| Electronic balance | AT261 | Mettler Toledo | M/EQM/106 |
| | AT250 | Mettler Toledo | M/EQM/151 |

(3) Synthesis

Example 1 Synthesis of 11-KA4-d7

15 mg of 11-OHA4-d7 was weighed out and was dissolved into 5 mL of dichloromethane. To the resultant solution, 1 mL of Dess-Martin Periodinane was added, and the mixture was stirred at room temperature for 30 minutes. After the stirring, 3 mL of saturated $NaHCO_3$ was added to the obtained solution. Then, the solution was extracted with 5 mL of dichloromethane, and an organic layer was thus obtained. The extraction with 5 mL of dichloromethane was further repeated two times. The organic layers were combined, dried over anhydrous sodium sulfate, and filtered. The solvent was evaporated from the filtrate under a nitrogen stream, and a residue was thus obtained. The residue was purified by TLC using chloroform:acetone (10:1), and the zone corresponding to 11-KA4 was scrapped and was extracted with ethyl acetate. The obtained ethyl acetate solution was evaporated under a nitrogen stream. A residue weighing 10.75 mg (71.2% yield in terms of 11-KA4-d7) was obtained. The residue was analyzed by NMR.

Example 2 Synthesis of 11-KT-d7

40 mg of 11-OHA4-d7 was weighed out and was dissolved into 10 mL of dichloromethane. To the resultant solution, 1 mL of Dess-Martin Periodinane was added, and the mixture was stirred at room temperature for 30 minutes. After the stirring, 6 mL of saturated $NaHCO_3$ was added to the obtained solution. Then, the solution was extracted with 6 mL of dichloromethane. The solution was further extracted with 10 mL of dichloromethane, and an organic layer was obtained. The extraction with 10 mL of dichloromethane was further repeated two times. The organic layers were combined, dried over anhydrous sodium sulfate, and filtered. The solvent was evaporated from the filtrate under reduced pressure, and a residue weighing 63.2 mg was obtained. The residue was purified by TLC using chloroform:acetone (10:1), and the zone corresponding to 11-KA4 was scrapped and was extracted with ethyl acetate. The obtained ethyl acetate solution was evaporated under a nitrogen stream. Thus, a residue weighing 37.5 mg (94.69% yield in terms of 11-KA4-d7) was obtained.

The residue obtained above was dissolved with 3 mL of benzene (super-dehydrated) and 2 mL of pyridine to give an 11-KA4-d7 solution, which was then ice cooled. Separately, 5 mg of $NaBH_4$ was dissolved into 5 mL of methanol (super-dehydrated), and the resultant solution was added dropwise to the 11-KA4-d7 solution over a period of 5 minutes. The reaction was performed by stirring the mixture under ice cooling for 30 minutes. After the completion of the reaction, 2 mL of glacial acetic acid was added to the reaction solution to decompose excess $NaBH_4$. The solvent of the reaction solution was evaporated under reduced pressure, and a residue weighing 63.2 mg was obtained. The residue was purified by TLC using chloroform:acetone (10:1), and the zone corresponding to 11-KT was scrapped and was extracted with ethyl acetate. The obtained ethyl acetate solution was evaporated under reduced pressure. Thus, a residue weighing 37.1 mg was obtained (98.4% yield in terms of 11-KT-d7 from 11-KA4-d7 as the raw material). The residue was analyzed by NMR.

Example 3 Synthesis of 11-OHT-d7

15 mg of 11-OHA4-d7 was dissolved with 1.5 mL of benzene (super-dehydrated) and 1 mL of pyridine to give an 11-OHA4-d7 solution. The solution was ice cooled. Separately, 5 mg of $NaBH_4$ was dissolved into 5 mL of methanol (super-dehydrated), and the resultant solution was added dropwise to the 11-OHA4-d7 solution over a period of 15 minutes. The reaction was performed by stirring the mixture under ice cooling for 1 hour. After the completion of the reaction, 2 mL of glacial acetic acid was added to decompose excess $NaBH_4$. The solvent was evaporated under reduced pressure. The residue was purified by TLC using benzene:acetone (3:1), and the zone corresponding to 11-OHT was scrapped and was extracted with ethyl acetate. The obtained ethyl acetate solution was evaporated under reduced pressure. Thus, a residue weighing 16.7 mg was obtained (110.6% yield in terms of 11-OHT-d7). The residue was analyzed by NMR.

(4) NMR Analysis

The compounds synthesized in Examples 1 to 3 were subjected to $^{1}H$-NMR and $^{13}C$-NMR measurements and further to accurate mass measurement. The results are described in tables below.

[Table 6]

TABLE 6

| Results of NMR analyses a 11-KA4-d7 and 11-OHA4-d7 | | | | |
|---|---|---|---|---|
| 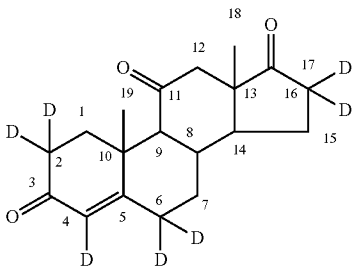 11-KA4-d7 | | | 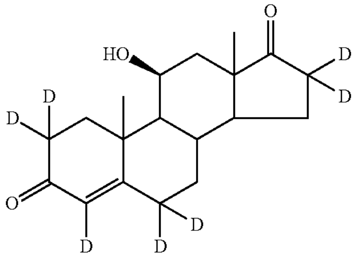 11-OHA4-d7 | |
| | 11-Ketoandrostenedione | | 11β-Hydroxyandrostenedione | |
| Positions | δc | $\delta_H$ (J in Hz) | δc | $\delta_H$ (J in Hz) |
| 1 | 34.6 | 1.64 (d, 13.2), 2.76 (d, 13.6) | 34.9 | 1.85 (d, 13.6), 2.18 (d, 13.2) |
| 3 | 199.7 | | 199.5 | |
| 5 | 167.8 | | 171.4 | |
| 7 | 30.8 | 1.29 (m), 2.13 (m) | 31.4 | 1.12 (t, 12.2), 2.11 (dd, 4.2, 13.0) |
| 8 | 49.9 | 1.90 (m) | 31.0 | 2.19 (m) |
| 9 | 63.4 | 1.93 (d, 11.2) | 56.8 | 1.01 (m) |
| 10 | 38.3 | | 39.3 | |
| 11 | 207.6 | | 68.1 | 4.47 (m) |
| 12 | 50.5 | 2.33 (d, 13.2), 2.50 (d, 12.4) | 41.41 | 1.50 (dd, 3.2, 14.4), 1.95 (dd, 2.2, 14.2) |
| 13 | 50.5 | | 46.8 | |
| 14 | 36.3 | 2.05 (m) | 52.5 | 1.24 (m) |
| 15 | 21.4 | 1.68 (t, 12.4), 2.14 (dd, 6.1, 13.2) | 21.6 | 1.65 (t, 12.2), 1.99 (dd, 6.0, 12.8) |
| 17 | 216.8 | | 219.2 | |
| 18 | 14.7 | 0.88 (s) | 15.9 | 1.16 (s) |
| 19 | 17.4 | 1.43 (s) | 21.1 | 1.47 (s) |
| High-resolution mass spectrometry (ESI-TOF): m/z $[M + H]^+$ | | | | |
| Data of $C_{19}H_{18}O_3D_7$: Calculated value: 308.2243 Measured value: 308.2236 | | | Data of $C_{19}H_{20}O_3D_7$: Calculated value: 310 2400 Measured value: 310 2392 | |

Recorded in $CDCl_3$

[Table 7]

TABLE 7

| Results of NMR analyses of 11-KT-d7 and 11-OHT-d7 | | | | |
|---|---|---|---|---|
| 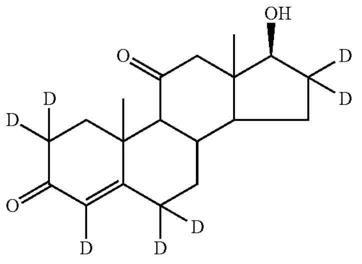 11-KT-d7 | | | 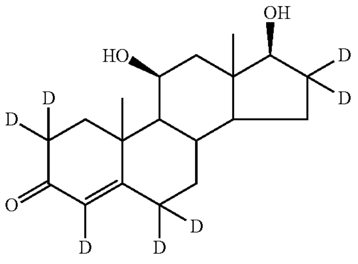 11-OHT-d7 | |
| | 11-Ketotestosterone[a] | | 11β-Hydroxytestosterone[b] | |
| Positions | δc | $\delta_H$ (J in Hz) | δc | $\delta_H$ (J in Hz) |
| 1 | 34.7 | 1.62 (d, 11.6) 2.76 (d, 14.0) | 34.3 | 1.85 (d, 13.2), 2.20 (d, 13.6) |
| 3 | 200.0 | | 201.3 | |
| 5 | 168.6 | | 175.3 | |
| 7 | 31.7 | 1.19 (t, 12.4), 1.96 (m) | 32.3 | 1.00 (m), 2.01 (m) |
| 8 | 37.5 | 1.96 (m) | 31.5 | 2.02 (m) |
| 9 | 62.9 | 1.88 (d, 1.04) | 56.7 | 0.96 (dd, 4.0, 812.0) |
| 10 | 38.2 | | 39.4 | |
| 11 | 208.9 | | 67.0 | 4.31 (m) |

TABLE 7-continued

| | | | | |
|---|---|---|---|---|
| 12 | 54.8 | 2.19 (d, 12.0), 2.440 (d, 12.4) | 45.6 | 1.22 (dd, 3.6, 14.0), 2.03 (dd, 2.2, 13.8) |
| 13 | 47.0 | | 41.9 | |
| 14 | 49.7 | 1.62 (m) | 52.8 | 1.22 (m) |
| 15 | 22.7 | 1.40 (t, 12.2), 1.76 (dd, 7.6, 12.4) | 22.8 | 1.35 (t, 12.2), 1.62 (dd, 7.0, 12.6) |
| 17 | 79.8 | 3.86 (s) | 81.4 | 3.51 (s) |
| 18 | 11.9 | 0.76 (s) | 12.5 | 1.01 (s) |
| 19 | 17.3 | 1.43 (s) | 20.0 | 1.47 (s) |
| High-resolution mass spectrometry (ESI-TOF) ; m/z $[M + H]^+$ | | | | |
| Data of $C_{19}H_{30}O_3D_7$: Calculated value: 310.2400<br>Measured value: 310.2397 | | | Data of $C_{19}H_{22}O_3D_7$: Calculated value: 312.2556<br>Measured value: 312.2555 | |

[a]Recorded in $CDCl_3$
[b]Recorded in $CD_3OD$

Based on the results described in Tables 6 and 7, the structures, labeled positions and labeling rates of the compounds synthesized in Examples 1 to 3 were determined. As a result, the compounds synthesized in Examples 1 to 3 were identified to be the objective stable isotope-labeled compounds 11-KA4-d7, 11-KT-d7 and 11-OHT-d7. Each of these compounds was free from Do molecules.

2. Measurement of Androgens (1)

The androgen concentrations in human plasma were measured using LC-MS/MS.

(1) Test Materials

The following materials were used.

(1)-1 Analyte Standards

Commercially available testosterone (T), dihydrotestosterone (DHT), 11β-hydroxyandrostenedione (11-OHA4), 11β-hydroxytestosterone (11-OHT), 11-ketoandrostenedione (11-KA4), 11-ketotestosterone (11-KT) and 11-keto-dihydrotestosterone (11-KDHT) were used as analyte standards.

(1)-2 Internal Standards (ISs)

Commercially available T-d3 (manufactured by CDN ISOTOPES), DHT-d3 (manufactured by CDN ISOTOPES) and 11-OHA4-d7 (manufactured by CDN ISOTOPES); and 11-KA4-d7, 11-KT-d7 and 11-OHT-d7 obtained in the above Examples 1 to 3 were used as internal standards.

(1)-3 Analyte Standard Reference Solutions and IS Reference Solutions

Each of the analyte standards and each of the ISs were each dissolved into acetonitrile to give 1 mg/mL stock solutions. Next, the stock solutions of the analyte standards were mixed together, and the mixture was diluted with acetonitrile. Thus, a 10 μg/mL analyte mixture stock solution was prepared. Similarly, the stock solutions of the ISs were mixed together, and the mixture was diluted with acetonitrile. Thus, a 10 μg/mL IS mixture stock solution was prepared. These mixture stock solutions were stored in a refrigerator.

Next, the analyte mixture stock solution was diluted with acetonitrile to give analyte standard reference solutions having a concentration of 0.01 to 20 ng/mL. Further, the IS mixture stock solution was diluted with acetonitrile to give an IS reference solution having a concentration of 10 ng/mL.

(1)-4 Human Plasma

Individual human plasmas (three male specimens and three female specimens) purchased from KAC (BIOPREDIC) were mixed in equal amounts to give a pooled plasma for use as the human plasma.

(1)-5 Reagents and Other Materials

Water was prepared by treating distilled water with the ultrapure water production equipment. Other reagents that were used were commercially available special grade reagents, HPLC standard reagents, or higher grade reagents.

(2) Test Method (2)-1 Blank Sample

50 μL of the water was added to a 1.5 mL PP tube containing 100 μL of acetonitrile, and the mixture was stirred to give a blank sample.

(2)-2 Zero Sample

50 μL of the water was added to a 1.5 mL PP tube containing 50 μL of acetonitrile and 50 μL of the IS reference solution, and the mixture was stirred to give a zero sample.

(2)-3 Calibration Standard Samples

50 μL of the water was added to 1.5 mL PP tube containing 50 μL of acetonitrile, 50 μL of the analyte standard reference solution and 50 μL of the IS reference solution, and the mixtures were stirred to give calibration standard samples.

(2)-4 Human Plasma Samples

50 μL of the IS reference solution and 50 μL of acetonitrile were added to 50 μL portions of the human plasma. Analyte concentration measurement samples (analyte concentration QC, n=3) were thus prepared.

Further, 50 μL of the IS reference solution and 50 μL of the analyte standard reference solution were added to 50 μL portions of the human plasma. Spike recovery test samples (low concentration QC: 0.1 ng/mL, medium concentration QC: 1 ng/mL, high concentration QC: 10 ng/mL, n=3 for each concentration) were thus prepared.

(2)-5 Liquid/Liquid Extraction (Salting-Out Assisted Liquid/Liquid Extraction)

50 μL of 5 mol/L ammonium acetate was added to each of the samples prepared above. The mixtures were stirred and centrifuged at 12,000 rpm for 2 minutes. The resultant supernatants were collected into sample tubes and were analyzed by LC-MS/MS. The LC-MS/MS conditions are described below.

(2)-6 LC-MS/MS (a) LC Section

Equipment: Nexera X2 (Shimadzu Corporation)

Analysis column: Kinetex 2.6 μm EVO C18 (2.6 μm, 4.6 mm I.D.×150 mm), (Phenomenex)

Column temperature: 45° C.

Mobile phases: A 0.05 vol % aqueous acetic acid solution, B acetonitrile (for LC/MS) (Wako)

[Table 8]

TABLE 8

| Gradient conditions | | | |
|---|---|---|---|
| Time (min) | A (%) | B (%) | Flow rate (mL/min) |
| 0.00 | 57 | 43 | 0.9 |
| 0.50 | 57 | 43 | 0.9 |
| 3.00 | 55 | 45 | 0.9 |
| 7.00 | 25 | 75 | 0.9 |
| 8.00 | ↓ | ↓ | 1.3 |
| 9.50 | 1 | 99 | 1.3 |
| 10.00 | 57 | 43 | 1.3 |
| 12.00 | 57 | 43 | 1.3 |
| 12.01 | 57 | 43 | 0.9 |
| 13.00 | 57 | 43 | 0.9 |

| | Time (min) | Position | |
|---|---|---|---|
| Valco valve | 0.5 | A | Introduced into MS |
| | 7.0 | B | Wasted |
| Autosampler cooler temperature | | | 10° C. |
| Column oven temperature | | | 45° C. |

| | Time (min) | Flow rate (mL/min) |
|---|---|---|
| Pump C (electrode washing solution) | 0.00 | 0.05 |
| 70 vol % methanol | 5.60 | 0.05 |
| | 5.61 | 0.01 |
| | 6.44 | 0.01 |
| | 6.45 | 0.05 |

Injection volume: 10 μL (b) LC Section

[Table 9]

TABLE 9

| Equipment: AB Sciex Qtrap 6500 (AB SCIEX) | |
|---|---|
| Ionization method | Positive ion ESI method (Turbo Spray Ion Drive) |
| CUR | 30 |
| GS1 | 88 |
| GS2 | 88 |
| IS | 5200 |
| TEM | 600° C. |
| CAD | 10 |
| EP | 10 |
| AnalysisQ 1, AnalysisQ 3 | Unit, low (0.1) |

[Table 10]

TABLE 10

| Measured ions | | | | | |
|---|---|---|---|---|---|
| Names of compounds | Precursor ions (m/z) | Product ions (m/z) | DP | CE | CXP |
| 11-KT_259 | 303.303 | 259.2 | 65 | 29 | 14 |
| 11-KA4_257 | 301.089 | 257.20 | 81 | 31 | 18 |
| 11-KDHT_287 | 305.158 | 286.80 | 116 | 21 | 38 |
| 11-OHT_269 | 305.160 | 269.20 | 106 | 21 | 18 |
| 11-OHA4_284 | 303.065 | 284.90 | 71 | 23 | 16 |
| T_97 | 289.173 | 97.00 | 80 | 26 | 11 |
| DHT_255 | 291.483 | 255.10 | 98 | 21 | 20 |
| I.S 11-KT-d7_266 | 310.197 | 266.20 | 111 | 33 | 16 |
| I.S 11-KA4-d7_264 | 308.200 | 264.10 | 100 | 33 | 30 |
| I.S 11-OHT-d7_276 | 312.196 | 275.90 | 86 | 23 | 32 |
| I.S 11-OHA4-d7_292 | 310.226 | 292.10 | 96 | 17 | 22 |

TABLE 10-continued

| Measured ions | | | | | |
|---|---|---|---|---|---|
| Names of compounds | Precursor ions (m/z) | Product ions (m/z) | DP | CE | CXP |
| I.S T-d3_97 | 292.065 | 96.80 | 150 | 27 | 12 |
| I.S DHT-d3_258 | 294.092 | 258.20 | 110 | 21 | 14 |

(c) Data Analysis Section

Control computer: OPTIPLEX 9010 (J3LPQ02 DELL)

Analysis computer: OPTIPLEX 9010 (3XKPQ02 DELL)

Analysis software: Analyst 1.6.2 (AB SCIEX)

(2)-7 Analysis

The peak area ratio (analyte/IS) was plotted against the added concentration to draw a calibration curve, and a $1/x^2$ weighted regression line was obtained.

The accuracy of the calibration standard sample relative to the added concentration was calculated from the following equation.

Accuracy (%) relative to added concentration=Inverse regression concentration of calibration standard sample/Added concentration×100

The precision was calculated from the following equation.

Precision (%)=Standard deviation/Average value×100

The theoretical value and accuracy in the spike recovery test were calculated from the following equations.

Theoretical value (ng/mL)=Average value of analyte concentrations+Added concentration Accuracy (%)=Average value/Theoretical value×100

(3) Results

Tables 11 to 14 below show the results obtained by measurements using as ISs the stable isotope-labeled compounds synthesized in Examples 1 to 3.

[Table 11]

TABLE 11

| Results of measurement of 11-KA4 concentration using 11-KA4-d7 from Example 1 11-Ketoandrostenedione (11-$KA_4$) Internal standard: 11-KA4-d7 | | | | |
|---|---|---|---|---|
| | Analyte concentration QC | Low concentration QC | Medium concentration QC | High concentration QC |
| Added concentration (ng/mL) of reference solution | 0 | 0.1 | 1 | 10 |
| Theoretical value (ng/mL) | — | 0.132 | 1.032 | 10.032 |
| Measured values (ng/mL) | 0.031 | 0.137 | 1.083 | 10.486 |
| | 0.035 | 0.142 | 1.050 | 10.567 |
| | 0.031 | 0.142 | 1.103 | 10.552 |
| Average value (ng/mL) | 0.032 | 0.140 | 1.078 | 10.535 |
| Standard deviation (ng/mL) | 0.002 | 0.003 | 0.027 | 0.043 |
| Precision (%) | 7.1 | 2.1 | 2.5 | 0.4 |
| Accuracy (%) | — | 106.3 | 104.5 | 105.0 |

[Table 12]

TABLE 12

Results of measurement of 11-KT concentration using 11-KT-d7 from Example 2
11-Ketotestosterone (11-KT)
Internal standard: 11-KT-d7

| | Analyte concentration QC | Low concentration QC | Medium concentration QC | High concentration QC |
|---|---|---|---|---|
| Added concentration (ng/mL) of reference solution | 0 | 0.1 | 1 | 10 |
| Theoretical value (ng/mL) | — | 0.388 | 1.288 | 10.288 |
| Measured values (ng/mL) | 0.291 | 0.362 | 1.337 | 11.002 |
| | 0.285 | 0.375 | 1.447 | 11.090 |
| | 0.289 | 0.386 | 1.358 | 11.126 |
| Average value (ng/mL) | 0.288 | 0.375 | 1.381 | 11.073 |
| Standard deviation (ng/mL) | 0.003 | 0.012 | 0.058 | 0.064 |
| Precision (%) | 1.2 | 3.2 | 4.2 | 0.6 |
| Accuracy (%) | — | 96.5 | 107.2 | 107.6 |

[Table 13]

TABLE 13

Results of measurement of 11-OHT concentration using 11-OHT-d7 from Example 3
11β-Hydroxytestosterone (11-OHT)
Internal standard: 11-OHT-d7

| | Analyte concentration QC | Low concentration QC | Medium concentration QC | High concentration QC |
|---|---|---|---|---|
| Added concentration (ng/mL) of reference solution | 0 | 0.1 | 1 | 10 |
| Theoretical value (ng/mL) | — | 0.178 | 1.078 | 10.078 |
| Measured values (ng/mL) | 0.077 | 0.183 | 1.109 | 10.297 |
| | 0.078 | 0.183 | 1.091 | 10.266 |
| | 0.079 | 0.184 | 1.084 | 10.583 |
| Average value (ng/mL) | 0.078 | 0.183 | 1.095 | 10.382 |
| Standard deviation (ng/mL) | 0.001 | 0.001 | 0.013 | 0.175 |
| Precision (%) | 1.3 | 0.4 | 1.2 | 1.7 |
| Accuracy (%) | — | 103.1 | 101.6 | 103.0 |

[Table 14]

TABLE 14

Results of measurement of 11-OHT concentration using T-d3 for reference
11β-Hydroxytestosterone (11-OHT) pr.269.20
Internal standard: T-d3 pr.96.80

| | Analyte concentration QC | Low concentration QC | Medium concentration QC | High concentration QC |
|---|---|---|---|---|
| Added concentration (ng/mL) of reference solution | 0 | 0.1 | 1 | 10 |
| Theoretical value (ng/mL) | — | 0.163 | 1.063 | 10.063 |
| Measured values (ng/mL) | 0.062 | 0.150 | 0.924 | 8.385 |
| | 0.062 | 0.150 | 1.158 | 8.502 |
| | 0.064 | 0.156 | 0.893 | 8.835 |
| Average value (ng/mL) | 0.063 | 0.152 | 0.992 | 8.574 |
| Standard deviation (ng/mL) | 0.001 | 0.003 | 0.145 | 0.234 |

TABLE 14-continued

Results of measurement of 11-OHT concentration using T-d3 for reference
11β-Hydroxytestosterone (11-OHT) pr.269.20
Internal standard: T-d3 pr.96.80

| | Analyte concentration QC | Low concentration QC | Medium concentration QC | High concentration QC |
|---|---|---|---|---|
| Precision (%) | 1.6 | 2.2 | 14.6 | 2.7 |
| Accuracy (%) | — | 93.3 | 93.3 | 85.2 |

From the above Tables 11 to 14, it has been demonstrated that the stable isotope-labeled compounds of Examples 1 to 3 used as ISs allow androgens to be measured in a highly selective and highly sensitive manner with simplified pretreatments. In particular, it has been shown that 11-OHT-d7 enables highly precise and highly sensitive measurement, compared to T-d3 in terms of reproducibility: precision and accuracy (Tables 13 and 14).

3. Measurement of Androgens (2)

The androgen concentrations in human plasma were measured using LC-MS/MS.

(1) Test Materials

The following materials were used.

(1)-1 Analyte Standards

Commercially available testosterone (T), dihydrotestosterone (DHT), 11β-hydroxyandrostenedione (11-OHA4), 11β-hydroxytestosterone (11-OHT), 11-ketoandrostenedione (11-KA4), 11-ketotestosterone (11-KT) and 11-keto-dihydrotestosterone (11-KDHT) were used as analyte standards.

(1)-2 ISs

Commercially available T-d3 (manufactured by Sigma-Aldrich), DHT-d3 (manufactured by Sigma-Aldrich) and 11-OHA4-d7 (manufactured by C/D/N ISOTOPES); and 11-KA4-d7, 11-KT-d7 and 11-OHT-d7 obtained in the above Examples 1 to 3 were used as ISs.

(1)-3 Analyte Standard Reference Solutions and IS Reference Solutions

Each of the analyte standards and each of IS were each dissolved into acetonitrile to give 1 mg/mL stock solutions. Next, the stock solutions of the analyte standards were mixed together, and the mixture was diluted with acetonitrile. Thus, a 10 μg/mL analyte mixture stock solution was prepared. Similarly, the stock solutions of IS were mixed together, and the mixture was diluted with acetonitrile. Thus, a 10 μg/mL IS mixture stock solution was prepared. These mixture stock solutions were stored in a refrigerator.

Next, the analyte mixture stock solution was diluted with acetonitrile to give analyte standard reference solutions having a concentration of 0.01 to 100 ng/mL. Further, the IS mixture stock solution was diluted with acetonitrile to give an IS reference solution having a concentration of 2 ng/mL.

(1)-4 Human Plasmas

Individual human plasmas (six male specimens and six female specimens) purchased from KAC Co., Ltd. (BIOPREDIC) were used as healthy human plasma.

Plasma from patients with benign prostatic hyperplasia (six male specimens), patients with prostate cancer (six male specimens), patients with castration-resistant prostate cancer (two male specimens), patients with polycystic ovary syndrome (six female specimens), patients with diabetes mellitus (five male specimens) and patients with diabetes mellitus nephropathy (seven male specimens), which were purchased from KAC Co., Ltd. (ProteoGenex), were used as patient-derived human plasmas.

(1)-5 Reagents and Other Materials

Water was prepared by treating distilled water with the ultrapure water production equipment. Other reagents that were used were commercially available special grade reagents, HPLC standard reagents, molecular biological standard reagents or higher grade reagents.

(2) Test Method (2)-1 Blank Sample

50 μL of the water was added to a 1.5 mL PP tube containing 100 μL of acetonitrile, and the mixture was stirred to give a blank sample.

(2)-2 Zero Sample

50 μL of the water was added to a 1.5 mL PP tube containing 50 μL of acetonitrile and 50 μL of the IS reference solution, and the mixture was stirred to give a zero sample.

(2)-3 Calibration Standard Samples

50 μL of the water was added to 1.5 mL PP tube containing 50 μL of each of the analyte standard reference solutions having a concentration of 0.01 to 100 ng/mL and 50 μL of the IS reference solution, and the mixtures were stirred to give calibration standard samples.

(2)-4 Human Plasma Samples

50 μL of acetonitrile and 50 μL of the IS reference solution were added to 50 μL of the healthy human plasmas and the patient-derived human plasmas. Human plasma samples were thus prepared.

(2)-5 Liquid/Liquid Extraction (Salting-Out Assisted Liquid/Liquid Extraction)

50 μL of 5 mol/L ammonium acetate was added to each of the samples prepared above. The mixtures were stirred and centrifuged at 4° C. and 13,000 rpm for 5 minutes. The resultant supernatants were collected into sample tubes and were analyzed by LC-MS/MS. The LC-MS/MS conditions are described below.

(2)-6 LC-MS/MS (a) LC Section

Equipment: Nexera X2 (Shimadzu Corporation)

Analysis column: Kinetex 2.6 μm EVO C18 (2.6 μm, 4.6 mm I.D.×150 mm), (Phenomenex)

Column temperature: 45° C.

Mobile phases: A 0.05 vol % aqueous acetic acid solution, B acetonitrile (for LC/MS) (Wako)

[Table 15]

TABLE 15

| HPLC gradient (linear) | | | |
|---|---|---|---|
| Time (min) | A (%) | B (%) | Flow rate (mL/min) |
| 0.00 | 57 | 43 | 0.9 |
| 0.50 | 57 | 43 | 0.9 |
| 3.00 | 55 | 45 | 0.9 |
| 7.00 | 25 | 75 | 0.9 |
| 8.00 | ↓ | ↓ | 1.3 |
| 9.50 | 1 | 99 | 1.3 |
| 10.00 | 57 | 43 | 1.3 |
| 12.00 | 57 | 43 | 1.3 |
| 12.01 | 57 | 43 | 0.9 |
| 13.00 | 57 | 43 | 0.9 |

Injection volume: 10 μL
Introduced into MS section in 0.5 to 7.0 min.

(b) LC Section

[Table 16]

TABLE 16

| Equipment: AB Sciex Qtrap 6500 (AB SCIEX) | |
|---|---|
| Ionization method | Positive ion ESI method |
| CUR | 30 |
| GS1 | 88 |
| GS2 | 88 |
| IS | 5200 |
| TEM | 600° C. |
| CAD | 10 |
| EP | 10 |
| Analysis Q1, Analysis Q3 | Unit, low |

[Table 17]

TABLE 17

| Measured ions | | | | |
|---|---|---|---|---|
| Names of compounds | Precursor ions (m/z $[M + H]^+$) | Product ions (m/z) | DP | CE |
| T | 289.173 | 97.00 | 80 | 26 |
| DHT | 291.483 | 255.10 | 98 | 21 |
| 11-OHA4 | 303.065 | 121.10 | 71 | 27 |
| 11-OHT | 305.160 | 269.20 | 106 | 21 |
| 11-KA4 | 301.089 | 257.20 | 81 | 31 |
| 11-KT | 303.303 | 259.2 | 65 | 29 |
| 11-KDHT | 305.160 | 105.00 | 116 | 35 |
| T-d3[a)] | 292.065 | 96.80 | 150 | 27 |
| DHT-d3[a)] | 294.092 | 258.20 | 110 | 21 |
| U-OHA4-d7[a)] | 310.226 | 292.10 | 96 | 17 |
| 11-OHT-d7[a)] | 312.196 | 275.90 | 86 | 31 |
| 11-KA4-d7[a)] | 308.200 | 264.10 | 100 | 33 |
| 11-KT-d7[a)] | 310.197 | 266.20 | 111 | 33 |

[a)]Internal standards (c) Data Analysis Section

Analysis computer: OPTIPLEX 9010 (DELL)

Analysis software: Analyst 1.6.2 (AB SCIEX)

(2)-7 Analysis (a) Calculation of Androgen Concentrations

The peak area ratio (analyte/IS) was plotted against the added concentration to draw a calibration curve, and a $1/x^2$ weighted regression line was obtained.

(b) Evaluation of Calibration Curves and Lower Limits of Quantification

Regarding the evaluation criteria of the calibration curves drawn (n=1 for each concentration), samples in which each of the calibration standard samples would have an accuracy of 80.0 to 120.0% at the lower limit of quantification and an accuracy of 85.0 to 115.0% at other than the lower limit of quantification would be a sample including at least ¾ of all the calibration standard samples, and the lower and upper limits of quantification.

(3) Results

The calibration curves of the analytes that were studied showed a good linearity. The lower limits of quantification were 0.01 ng/mL for T, DHT, 11-OHT, 11-KA4 and 11-KT, 0.02 ng/mL for 11-OHA4, and 0.1 ng/mL for 11-KDHT (Table 18).

When the stable isotope-labeled form of each of the analytes was used as IS, the precision and the accuracy were improved compared to case that T-d3 was used as IS (here, 11-KDHT had no stable isotope-labeled form and therefore was analyzed using 11-KT-d7 as IS), similarly to the results in the above item “2. Measurement of androgens (1)”. The androgen concentrations in the plasma were determined using the stable isotope-labeled forms of the analytes as IS.

The average values and the standard deviations of the androgen concentrations in the plasma were calculated using Microsoft Excel 2016 (Microsoft Corporation), the results being described in Table 19 below. When the individual values were below the lower limit of quantification (LLOQ), the average value and the standard deviation were calculated or indicated according to the following rules.

When less than half of the samples were below LLOQ, the average value alone was calculated assuming that LLOQ was 0.

When half or more of the samples were below LLOQ, the average value and the standard deviation were not calculated and were indicated as NC (not calculated).

[Table 18]

TABLE 18

Accuracies of analytes in calibration standard samples

| Concentration (ng/mL) of calibration standard sample | Accuracies (%) T | DHT | 11-0HA4 | 11-0HT | 11-KA4 | 11-KT | 11-KDHT |
|---|---|---|---|---|---|---|---|
| 0.01 | 98.1 | 95.2 | No Peak | 95.8 | 98.0 | 99.8 | No Peak |
| 0.02 | 103.1 | 109.6 | 101.8 | 109.0 | 103.7 | 99.3 | No Peak |
| 0.1 | 104.1 | 99.1 | 90.4 | 95.9 | 99.4 | 106.6 | 101.7 |
| 0.2 | 98.3 | 102.0 | 101.7 | 102.0 | 104.5 | 99.1 | 96.8 |
| 1.0 | 99.9 | 100.2 | 98.1 | 99.6 | 98.2 | 97.9 | 98.4 |
| 2.0 | 99.8 | 98.8 | 102.9 | 99.0 | 98.1 | 101.0 | 100.7 |
| 10.0 | 100.9 | 102.3 | 105.1 | 100.5 | 101.1 | 99.5 | 102.1 |
| 20.0 | 101.3 | 95.8 | 100.8 | 100.0 | 99.4 | 99.2 | 101.4 |
| 100.0 | 94.5 | 97.0 | 99.3 | 98.2 | 97.6 | 97.7 | 98.9 |
| Coefficient of correlation | 1.000 | 0.999 | 0.997 | 0.999 | 1.000 | 1.000 | 0.985 |

[Table 19]

TABLE 19

Androgen concentrations in healthy human plasmas and diseased patient plasmas

| Samples | Androgen concentrations (ng/mL) in plasmas T | DHT | 11-0HA4 | 11-0HT | 11-KA4 | 11-KT | 11-KDHT |
|---|---|---|---|---|---|---|---|
| BPH | 5.08 ± 1.07 | 0.33 ± 0.11 | 1.79 ± 0.61 | 0.18 ± 0.06 | 0.08 ± 0.06 | 0.56 ± 0.21 | NC |
| PCa | 3.23 ± 2.02 | 0.22 ± 0.12 | 1.67 ± 0.63 | 0.16 ± 0.07 | 0.08 ± 0.03 | 0.43 ± 0.16 | NC |
| CRPC [a)] | 1.71 | 0.16 | 2.02 | 0.20 | 0.15 | 0.45 | NC |
| PC0S | 0.44 ± 0.22 | 0.07 ± 0.04 | 1.32 ± 0.59 | 0.14 ± 0.08 | 0.09 ± 0.03 | 0.47 ± 0.22 | NC |
| DM | 2.52 ± 0.14 | 0.13 ± 0.04 | 2.45 ± 0.24 | 0.15 ± 0.03 | 0.07 ± 0.01 | 0.37 ± 0.13 | NC |
| DMN | 3.27 ± 2.11 | 0.19 ± 0.25 | 1.66 ± 0.57 | 0.09 ± 0.08 | 0.07 ± 0.01 | 0.31 ± 0.16 | NC |
| Male | 5.15 ± 1.08 | 0.38 ± 0.23 | 0.60 ± 0.62 | 0.11 ± 0.08 | 0.03 ± 0.01 | 0.27 ± 0.17 | NC |
| Female | 0.22 ± 0.13 | 0.08 ± 0.04 | 0.51 ± 0.24 | 0.06 ± 0.03 | 0.03 ± 0.01 | 0.30 ± 0.12 | NC |

[a)] There were only two CRPC specimens and thus only the average value thereof was indicated.

Figure 2:
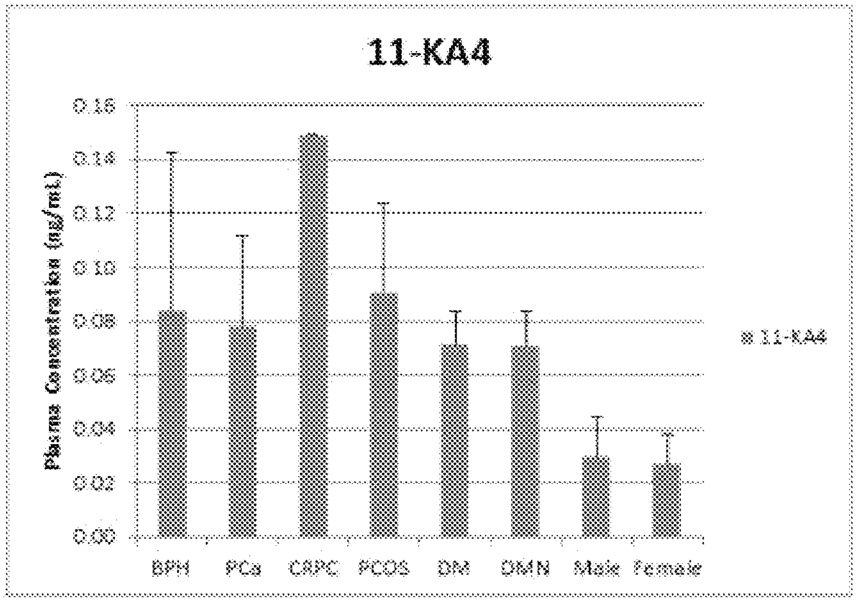
FIG. 2 shows the plasma 11-KA4 concentrations in healthy human and patients with diseases.
Figure 3:
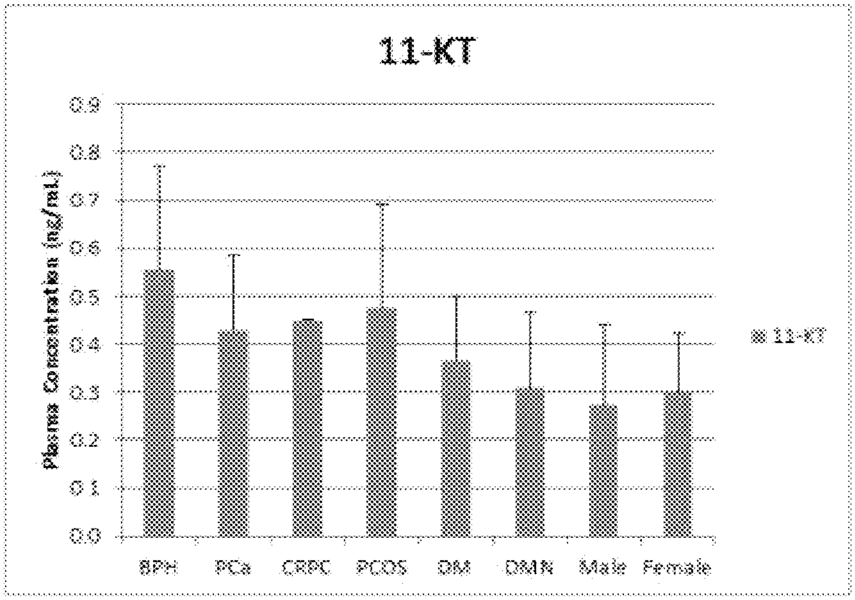
FIG. 3 shows the plasma 11-KT concentrations in healthy human and patients with diseases.
Figure 4:
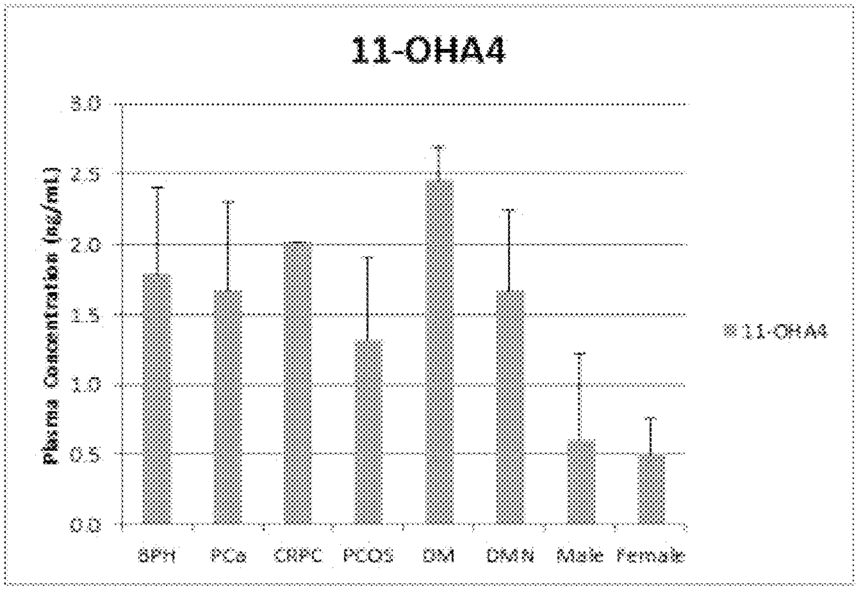
FIG. 4 shows the plasma 11-OHA4 concentrations in healthy human and patients with diseases.

The concentrations of the androgens were measured by the measurement method of the invention with respect to the healthy male and female plasma and the plasma from patients with benign prostatic hyperplasia (BPH), prostate cancer (PCa), castration-resistant prostate cancer (CRPC), polycystic ovary syndrome (PCOS), diabetes mellitus (DM) and diabetes mellitus nephropathy (DMN) (Table 19 and FIGS. 1 to 4). High concentrations of 11-KA4 were detected in the plasma from the BPH, PCa, CRPC, PCOS, DM and DMN patients as compared to the healthy subject plasma, and the concentration was particularly high in the CRPC plasma. Further, the 11-OHA4 concentrations were higher in the plasma from the BPH, PCa, CRPC, PCOS, DM and DMN patients as compared to the healthy subject plasma.

The 11-KT concentrations in the plasma from the BPH, PCa and CRPC patients were 1.6 to 2.1 times higher than in the healthy male subjects. The concentration of T and that of 11-KT in the plasma from the PCOS patients were 2.0 times and 1.8 times, respectively, higher than in the healthy female subjects, which reflected the PCOS hyperandrogenism. The T concentrations in the plasma from the DM and DMN male patients were lower than in the healthy male subjects.

As demonstrated above, the plasma from the BPH, PCa, CRPC, PCOS, DM and DMN patients contained higher levels of 11-OHT, 11-KA4, 11-KT and 11-OHA4. These results suggest that 11-OHT, 11-KA4, 11-KT and 11-OHA4 may be used as biomarkers for these diseases. In particular, 11-KA4 will be effective as a biomarker, and is considered to be especially able to differentiate CRPC (castration-resistant prostate cancer) and PCa (prostate cancer).

The foregoing has demonstrated that a method has been developed which is capable of more accurate quantitative measurement of androgens in plasma by using stable isotope-labeled forms of the analytes as IS. The results of the measurement of healthy human plasma and plasma of patients by disease using the present measurement method have shown that 11-OHT, 11-KA4, 11-KT and 11-OHA4 are potential biomarkers for BPH, PCa, CRPC, PCOS, DM and DMN.

INDUSTRIAL APPLICABILITY

The measurement method of the present invention can detect the presence or absence of androgens in samples, and can determine the amounts thereof. Thus, the measurement method allows androgens to be used as biomarkers for the diagnosis of particular diseases.

The present invention may be used in fields such as, for example, medicine, pharmacy, biochemistry, public health and food inspection.

The invention claimed is:

1. A stable isotope-labeled compound selected from [2,2,4,6,6,16,16-$D_7$]11-ketoandrostenedione, represented by Formula (I); [2,2,4,6,6,16,16-$D_7$]11-ketotestosterone, represented by Formula (II); and [2,2,4,6,6,16,16-$D_7$]11β-hydroxytestosterone, represented by Formula (III):

(I)

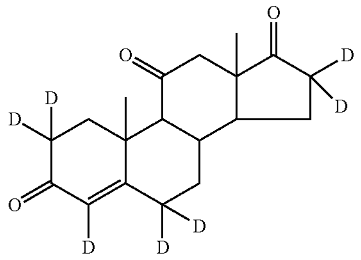

(II)

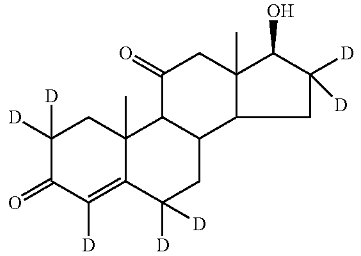

(III)

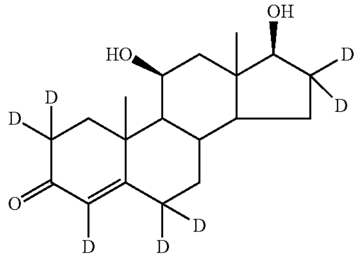

, wherein D denotes deuterium.

2. A method for measuring an androgen in a sample by liquid chromatography mass spectrometry, comprising a step of using the stable isotope-labeled compound described in claim 1 as an internal standard.

3. The method according to claim 2, wherein the androgen is at least one selected from the group consisting of 11-ketoandrostenedione, 11-ketotestosterone, 11β-hydroxytestosterone, 11-ketodihydrotestosterone, testosterone and dihydrotestosterone.

4. A method for diagnosis of at least one of benign prostatic hyperplasia, prostate cancer, castration-resistant prostate cancer, polycystic ovary syndrome, diabetes mellitus and diabetes mellitus nephropathy, the method comprising measuring at least one of 11-ketoandrostenedione, 11-ketotestosterone and 11β-hydroxytestosterone in a sample using the method described in claim 2.

5. A method for diagnosis of prostate cancer or castration-resistant prostate cancer, the method comprising measuring 11-ketoandrostenedione in a sample using the method described in claim 2.

6. A method for measuring an androgen in a sample by liquid chromatography mass spectrometry, wherein the method comprises the following procedures:

Procedure 1: dissolving an androgen as an analyte into a solvent to prepare an analyte standard reference solution;

Procedure 2: dissolving the stable isotope-labeled compound described in claim 1 into a solvent to prepare an internal standard reference solution;

Procedure 3: combining a sample of interest together with the internal standard reference solution prepared in Procedure 2 and a solvent to prepare an analyte concentration measurement sample;

Procedure 4: combining the sample of interest together with the analyte standard reference solution prepared in Procedure 1 and the internal standard reference solution prepared in Procedure 2 to prepare a spike recovery test sample; and Procedure 5: analyzing each of the analyte concentration measurement sample prepared in Procedure 3 and the spike recovery test sample prepared in Procedure 4 by liquid chromatography mass spectrometry.

7. The method according to claim 6, wherein the concentration of the androgen in the analyte standard reference solution described in Procedure 1 is 0.01 to 20 ng/mL.

8. The method according to claim 6, wherein the concentration of the stable isotope-labeled compound in the internal standard reference solution described in Procedure 2 is 10 ng/mL.

9. A method for producing a stable isotope-labeled compound described in claim 1, comprising any one step selected from the group consisting of the following steps:

Step 1: subjecting a compound represented by Formula (IV) below:

(IV)

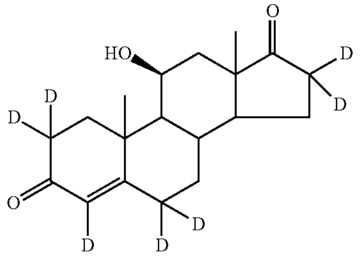

to an oxidation reaction to give [2,2,4,6,6,16,16-$D_7$]11-ketoandrostenedione, a compound represented by Formula (I) below:

(I)

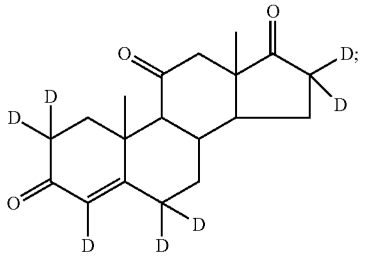

Step 2: dissolving the compound of Formula (I) above into a super-dehydrated solvent and then subjecting the compound of Formula (I) to a reduction reaction using a reducing agent dissolved in a super-dehydrated solvent to give [2,2,4,6,6,16,16-$D_7$]11-ketotestosterone, a compound represented by Formula (II) below:

(II)
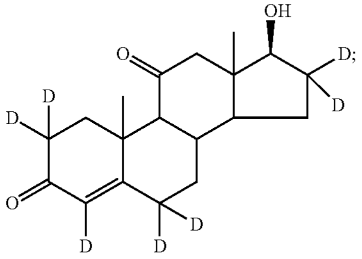
and
Step 3: dissolving the compound of Formula (IV) above into a super-dehydrated solvent and then subjecting the compound of Formula (IV) to a reduction reaction using a reducing agent dissolved in a super-dehydrated solvent to give [2,2,4,6,6,16,16-$D_7$]11β-hydroxytestosterone, a compound represented by Formula (III) below:
(III)
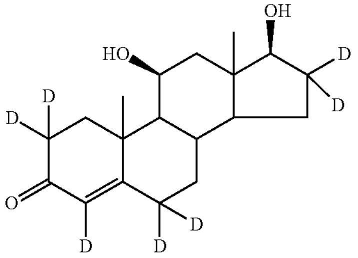
;
wherein in the above formulae, D denotes deuterium.
* * * * *